United States Patent [19]

Christenson et al.

[11] Patent Number: 5,371,069
[45] Date of Patent: * Dec. 6, 1994

[54] ORGANOLEPTIC COMPOSITIONS

[75] Inventors: Philip A. Christenson, Midland Park; Paul J. Riker, Lodi, both of N.J.; Denise A. Anderson, Brooklyn, N.Y.; John M. Yurecko, Jr., Dayton, N.J.

[73] Assignee: Giuaudan-Roure Corporation, Clifton, N.J.

[*] Notice: The portion of the term of this patent subsequent to Sep. 1, 2009 has been disclaimed.

[21] Appl. No.: 870,104

[22] Filed: Apr. 17, 1992

Related U.S. Application Data

[63] Continuation of Ser. No. 626,354, Dec. 12, 1990, abandoned.

[51] Int. Cl.$^5$ .............. A51K 7/46; C07D 317/26
[52] U.S. Cl. .................... 512/12; 512/13; 549/435; 549/448; 549/450; 549/454
[58] Field of Search ........... 549/435, 448, 450, 454; 514/467; 512/12, 13

[56] References Cited

U.S. PATENT DOCUMENTS

| | | | |
|---|---|---|---|
| 3,625,709 | 12/1971 | Mitchell | 99/140 R |
| 3,818,107 | 6/1974 | Yolles | 426/3 |
| 3,857,964 | 12/1974 | Yolles | 426/3 |
| 4,001,438 | 1/1977 | Marmo et al. | 426/96 |
| 4,119,106 | 10/1978 | Grubbs et al. | 131/17 R |
| 4,199,593 | 4/1980 | Mues et al. | 549/435 |
| 4,253,473 | 3/1981 | Marino et al. | 131/2 |
| 4,280,011 | 7/1981 | DeSimone | 568/603 |
| 4,435,315 | 3/1984 | Conrad et al. | 252/522 R |
| 4,538,627 | 9/1985 | Chan et al. | 131/276 |
| 4,538,628 | 9/1985 | Podraza | 131/277 |
| 4,540,004 | 9/1985 | Podraza et al. | 131/277 |
| 4,578,486 | 3/1986 | Podraza et al. | 549/379 |
| 4,607,118 | 8/1986 | Grubbs et al. | 560/60 |
| 4,690,157 | 9/1987 | Podraza et al. | 131/276 |
| 4,701,282 | 10/1987 | Chan et al. | 260/410.9 R |
| 4,880,775 | 11/1989 | Christenson et al. | 512/12 |
| 5,139,793 | 8/1992 | Johnson et al. | 426/3 |
| 5,144,048 | 9/1992 | Christensen et al. | 549/435 |

FOREIGN PATENT DOCUMENTS 236566 9/1987 European Pat. Off. ............ 549/450

OTHER PUBLICATIONS

C.A. 109, 149174n, (1988).
C.A. 107, 39666z, (1987).
CA 104, 129673s, (1985).
CA 103, 22349t (1985).
C.A. 100, 102847g, (1984).
CA 90, 38454 x, (1979).
CA 69, 66755f, (1968)
CA 108, 149914G, (1988).
CA 112, 35666 e, (Jan. 29, 1990).

*Primary Examiner*—C. Warren Ivy
*Assistant Examiner*—Ba K. Trinh
*Attorney, Agent, or Firm*—Richard R. Muccino

[57] ABSTRACT

The present invention provides organoleptic compositions which upon thermolyis, hydrolysis or both, release an odorant molecule. They find utility, for example, in tobacco, in tobacco paper, and as additives to food, beverages or gum. The compositions contain one or more dicarboalkoxy dioxolane derivatives having the following formula:

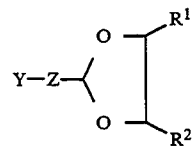

wherein $R^1$ and $R^2$ are, independently, $-CO_2R^3$ wherein $R^3$ is $-H_3$ or lower alkyl, provided that in at least one of $R^1$ and $R^2$, $R^3$ is lower alkyl; wherein Z is a direct bond, or $-CH=C(R^4)-$; where $R^4$ is $-H$ or alkyl group; and Y is

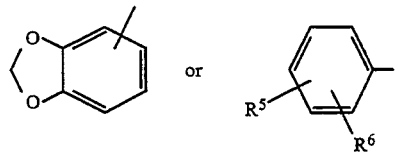

where $R^5$ and $R^6$ are independently $-H$, lower alkyl or $-OR^7$ where $R^7$ is $-H$ or lower alkyl.

4 Claims, No Drawings

ORGANOLEPTIC COMPOSITIONS

This is a continuation application of copending patent application Ser. No. 07/626,354, filed Dec. 12 1990, now abandoned.

FIELD OF THE INVENTION

The present invention relates to organoleptic compositions. More particularly, it relates to flavor and fragrance compositions which contain one or more dicarboalkoxy dioxolane derivatives which are normally odorless but which upon thermolysis, hydrolysis or both, release an odorant molecule.

CROSS REFERENCE TO RELATED APPLICATIONS

Attention is directed to copending, commonly assigned U.S. application Ser. No. 395,628, filed Aug. 18, 1989, and entitled "NOVEL CYCLIC ACETALS" as well as to U.S. application Ser. No. [Attorney Docket No. 1301], filed [herewith], and entitled "DICARBOALKOXY DIOXOLANE DERIVATIVES."

BACKGROUND OF THE INVENTION

Flavor additives have long been used to flavor a wide variety of consumer products, particularly tobacco products, foodstuffs, and gums. Flavor additives in such products may be used to mask or attenuate undesirable flavors or odorants, and to enhance existing flavors or odors, or to provide additional flavors or odors not initially present in the consumer product.

A principal strategy currently employed to impart flavors or odors to consumer products is the admixing of the flavorant chemicals within a matrix that slows or prevents their release until the product is pyrolyzed, heated, masticated or wetted. Alternatively, the flavoring chemical may be covalently bound to an auxilliary component to form a higher molecular weight molecule of low volatility. The flavorant is then released upon pyrolysis, heating or solvolysis of the tobacco or food product. For example, European patent 186, 502 describes the use of a plastic capsule that releases flavorants when mechanically crushed.

U.S. Pat. No. 4,001,438 describes flavor compositions for use in orally utilizable compositions which may be either chewing gum compositions, chewable medicinal tablets, chewing tobacco or toothpaste. The flavor is controllably released from the flavor compositions over an extended period of time under hydrolytic conditions.

U.S. Pat. No. 4,253,473 describes smoking tobacco compositions or substitute smoking tobacco compositions which upon smoking release substantially evenly and uniformly over an extended period of time.

U.S. Pat. No. 3,818,107 describes a chewing gum containing a flavor release composition comprising polymer backbones with flavor groups appended thereto. The flavor moieties are released from the polymer backbone by hydrolysis which is achievable by mastication of chewing gums containing the flavor groups.

As an alternative method, the flavoring chemicals may be covalently bound to an auxilliary component to form a higher molecular weight molecule of low volatility. The flavorant is released upon pyrolysis, heating or solvolysis of the tobacco or food product.

In general, inventions employing the second strategy use an ester or carbonate linkage of a higher molecular weight molecule to an alcoholic flavor molecule. In such a system, a flavor molecule is covalently bound to a polymer and may be depicted by the following generalized structure:

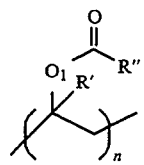

wherein R' represents a lower alkyl group such as methyl, R" represents a flavorant radical such as menthyl and n is an integer of from 2 to 10,000. This approach has been demonstrated in a number of U.S. Patents.

For example, U.S. Pat. No. 4,212,310 describes different flavored smoking tobacco products wherein some of the products contain an alcohol flavorant-release composition which delivers the flavor of the alcohol upon pyrolysis.

U.S. Pat. No. 4,119,106 describes alcohol flavorant-release polymeric derivatives which are designed to enhance tobacco smoke by releasing an alcohol flavorant to tobacco smoke without wasting the natural flavor of the resultant main stream tobacco smoke.

U. S. Pat. Nos. 4,578,486 and 4,538,628 describe smoking tobacco compositions which contain dioxane diester flavorant-release additives. When subjected to normal smoking conditions such as cigarettes, the diester additive decomposes to release a volatile pyrolysis (alcohol or phenol) component which provides flavor-enhancing properties to the mainstream smoke and enhances the aroma of the sidestream smoke.

U.S. Pat. Nos. 4,701,282, 4,538,627, and 4,540,004 describe the use of ketoester or carbonate compounds as flavorant additives which under cigarette smoking conditions pyrolyze to release flavorants which enhance the flavor of the mainstream smoke and the aroma of sidestream smoke.

Acetals have also been used as vehicles to covalently bind aldehyde flavorants. For example, U.S. Pat. 4,296,137 describes the use of 1-ethoxy-1-ethanol acetate as a flavor or fragrance enhancer of a wide variety of consumable materials. The 1-ethoxy-1-ethanol acetate compound has the ability to liberate acetaldehyde in smoking tobacco.

U. S. Pat. No. 4,280,011 describes the use of acetals as aldehyde generators in foodstuff applications.

U.S. Pat. No. 3,625,709 describes food flavoring and aroma enhancers consisting of acetaldehyde combined with carbohydrates to form compositions which release acetaldehyde when combined with hot water or with cold water.

U.S. Pat. No. 3,857,964 describes controlled release flavor compositions useful in flavor compositions which comprise flavor particles formed from a dispersion of flavor acetal or ketal in polymeric binders. The controlled release flavor compositions have multiple means of control, one of which is the hydrolysis of the flavor acetal or ketal. These controlled release flavor compositions are useful in chewing gums.

U.S. Pat. Nos. 4,690,157 and 4,607,118 describe tobacco compositions which contain flavor release additives which, under cigarette smoking conditions, pyrolyze in a "retro-aldol" fragmentation reaction into products which enhance the flavor and aroma of the cigarette smoke.

SUMMARY OF THE INVENTION

The present invention provides organoleptic compositions which contain one or more compounds which, upon thermolysis, hydrolysis or both, release an odorant molecule. Exemplary of applications for the compositions of the present invention are tobacco products such as cigarettes and tobacco paper; foodstuffs such as cakes, cookies, crackers, breads and cereals; beverages such as tea and coffee; and gums such as chewing gums.

These compositions contain a dicarboalkoxy dioxolane derivative of Structure I:

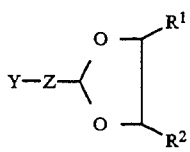

wherein $R^1$ and $R^2$ are, independently, $-CO_2R^3$ wherein $R^3$ is $-H_3$ or lower alkyl, provided that in at least one of $R^1$ and $R^2$, $R^3$ is lower alkyl; wherein Z is a direct bond, or $-CH=C(R^4)-$; where $R^4$ is $-H$ or an alkyl group; and Y is

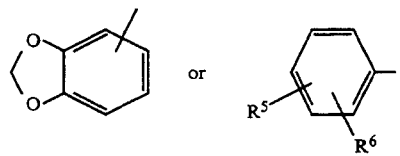

where $R^5$ and $R^6$ are independently $-H$, lower alkyl or $-OR^7$ where $R^7$ is $-H$ or lower alkyl.

The compound or compounds are present in an amount such that, when subjected to hydrolysis, pyrolysis or both, provide an organoleptically effective level of flavor or aroma.

DEFINITIONS

As used throughout this specification, the term "organoleptic" refers to compounds which stimulate the sense of smell or taste, and are thus perceived as having a characteristic odor, flavor or both.

The terms "odor," "fragrance," and "smell" are used interchangeably whenever a compound is referred to as an organoleptic which is intended to stimulate the sense of smell. The terms "flavor," "flavoring," and "flavorant" are also used interchangeably whenever an organoleptic compound is referred to which is intended to stimulate the sense of taste.

An "organoleptically effective amount" is a level or amount of a compound or compounds of the invention present in a material at which the incorporated compound or compounds exhibit a sensory effect.

The terms "tobacco," and "tobacco substitutes" are used in the conventional sense and include smokable as well as non-smokable forms in which tobacco is regularly used, e.g., cigarettes, snuff, chewable compositions and the like.

Alkyl (including the alkyl portion of alkoxy and alkylthio)—a branched or unbranched saturated carbon chain containing 1 to 12 carbon atoms with lower alkyl representing a chain containing 1 to 6 carbon atoms.

DESCRIPTION OF THE INVENTION

The organoleptic compositions of the invention contain one or more compounds which can be readily prepared by methods known to those skilled in the art. Exemplary methods are set forth in the example section below. The usual method involves condensation of an aldehyde with diethyl tartrate (or some other lower alkyl tartrate) in an inert solvent in the presence of an acid catalyst. During the condensation water is usually removed.

Either protic or Lewis acids may be used. Some acids which may be used are p-toluenesulfonic acid, sulfuric acid, phosphoric acid, hydrochloric acid, methanesulfonic acid, pyridinium p-toluenesulfonate, ferric chloride, acidic clay, acidic ion exchange resins, zinc chloride and titanium tetrachloride.

Preferred acids include p-toluenesulfonic acid, methanesulfonic acid and pyridinium p-toluenesulfonate. The most preferred acid is p-toluenesulfonic acid.

A variety of inert solvents may be used such as toluene, benzene, xylene, cyclohexane, hexane, dimethyl formamide, chlorobenzene and dichloroethane. The preferred solvents are toluene, xylene or dimethylformamide. The most preferred solvents are toluene and dimethylformamide.

The water formed in the reaction may be removed by azeotropic distillation or by interaction with a water scavenging agent such as a trialkyl orthoformate (alkyl is C1 to C5 and is usually the same as the lower alkyl in the tartrate), molecular sieves, sodium sulfate and the like.

In addition, the compounds may be prepared by first converting the aldehydes of the invention to the corresponding di-lower alkyl acetals (lower alkyl should be the same as the lower alkyl in the desired tartrate). Reaction of the acetals with a dialkyl tartrate under the conditions similar to that used when starting with an aldehyde will result in formation of the compounds.

The organoleptic compositions may be used as flavorants in tobacco compositions, as sustained release odorants to mask or enhance the odors of burning tobacco products, in beverages, in microwaveable foods, and in the preparation of chewing gums.

The compounds used in the compositions are virtually odorless and tasteless under normal temperatures and atmospheric conditions, i.e., about 10–50 degrees Celcius and about 20 to 100% relative humidity, and exist as stable solids. However, when heated to higher temperatures, i.e., about 70 to about 300 degrees Celcius, in the presence of moisture or steam, they undergo a transformation in which the aldehyde is released.

Illustrative examples of preferred species are shown below:

(4R, 5R)-2-(3-Ethoxy-4-hydroxy-phenyl)-4,5-dicarboethoxy-1,3-dioxolane

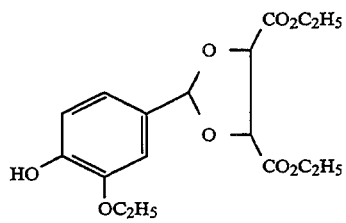

(4R,5R)-2-(3-Methoxy-4-hydroxy-phenyl)-4,5-dicarbo-
ethoxy-1,3-dioxolane

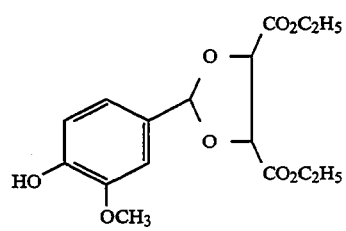

(4R,5R)-2-(4-Methoxyphenyl)-4,5-dicarboethoxy-1,3-
dioxolane

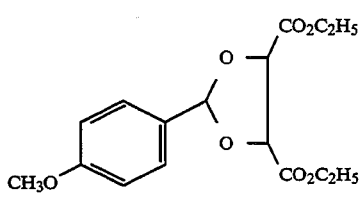

(4R,5R)-2-(4-Methylphenyl)-4,5-dicarboethoxy-1,3-
dioxolane

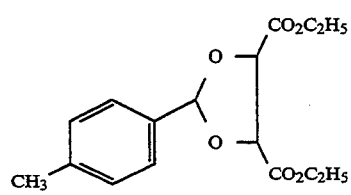

(4R,5R)-2-(2-phenyl-1-ethenyl)-4,5-dicarboethoxy-1,3-
dioxolane

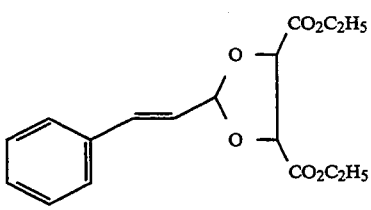

(4R,5R)-2-(3,4-Methylenedioxyphenyl)-4,5-dicarboe-
thoxy-1,3-dioxolane

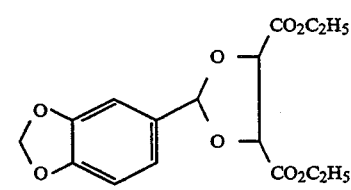

(4R, 5R) -2-(3-Methoxy-4-hydroxy-phenyl)-4,5-dicar-
bomethoxy-1,3-dioxolane

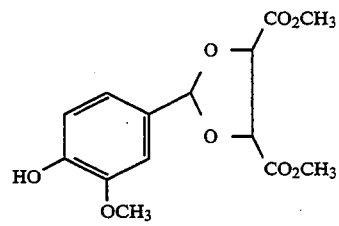

(E)-(4R,5R)-2-(1-Hexyl-2-phenyl-1-ethenyl)-4,5-dicar-
bomethoxy-1,3-dioxolane

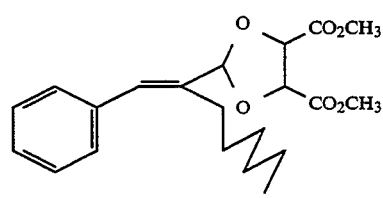

(E)-(4R,5R)-2-(1-Hexyl-2-phenyl-1-ethenyl)-4,5-dicar-
boethoxy-1,3-dioxolane

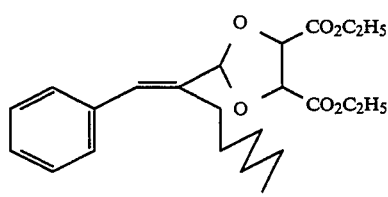

The compounds useful in the compositions of the present invention are not limited to any particular stereoisomer and all possible stereoisomers are included within the scope of the invention.

Methods of preparation are described in the following publications:

P. Kocienski, et al., Synthetic Comm., 1984,14, pp.1087–1092

L. A. Paguette et al., J. Org. Chem., 1985,50, pp.5528–5533

M. Demuth et al., J. Am. Chem. Soc., 1986,108, pp. 4149–4154

Y. Masaki et al., Chem. Letters, 1983, pp. 1835–1836

H. Yamamoto et al., J. Am. Chem. Soc., 1985,107, pp.8254–8256

T. W. Greene, "Protective Groups in Organic Synthesis," Chapter 4, John Wiley & Sons, New York, 1981

Compositions of the present invention contain these compounds individually or in combination in an amount effective to enhance a characteristic flavor or odor of a material. More commonly, however, the compounds are mixed with other flavor or fragrance components in an amount sufficient to provide the desired flavor or odor characteristic.

The amount required to produce the desired, overall effect varies depending upon the particular compound chosen, the product in which it will be used, and the particular effect desired.

For example, depending upon the selection and concentration of the compound or compounds chosen, when added either singly or as a mixture to cigarette tobacco at levels ranging from about 5 ppm to about 50,000 ppm it tends to enhance the smoking flavor, mask undesirable smoking odor or both. An important property of these compounds is that the flavorant or odorant is covalently bound as a non-volatile compound and it is only when the tobacco product is ignited and burns that the flavorant or odorant is released.

These compounds are present either separately or as a mixture at levels ranging from about 5 ppm to about 50,000 ppm by weight on the media enclosing the tobacco which serves to incorporate the odorant or flavorant in the side-stream smoke as the tobacco product burns. Air borne flavorants, odorants or both along with other combustion products are thus introduced. This newly formed odorant or flavorant serves to enhance or mask the smoking odors depending upon selection and use levels of the compounds.

These compounds are particularly useful in the flavoring and aromatizing of certain cooked foods. For example, the compounds either singly or as a mixture added to cake batter impart an appropriate baking aroma to the cake as it is heated, as well as impart a flavor to the finished product. Typically, the compounds are employed at levels ranging from about 0.05 to about 5.00%.

The flavor of chewing gum may be enhanced by the addition of these compounds. A selected compound or mixture of compounds are kneaded into a gum base at levels ranging from about 0.1 to about 10.0% by weight. The appropriate flavors are released in the resulting gum upon mastication.

These compositions may, when used as additives to a foodstuff or tobacco product, contain or be added along with other ingredients. Such other ingredients include emulsifiers, carriers, binders, sweeteners, stabilizers, buffers and solvents.

The following examples serve to illustrate embodiments of the invention and the advance over the prior art. The examples are presented to illustrate and not to limit the scope of the invention.

All parts, proportions, percentages, and ratios used in the examples are by weight unless otherwise indicated.

EXAMPLES

Example 1

(4R,5R)-2-(3-Ethoxy-4-hydroxy-phenyl)-4,5-dicarboethoxy-1,3-dioxolane

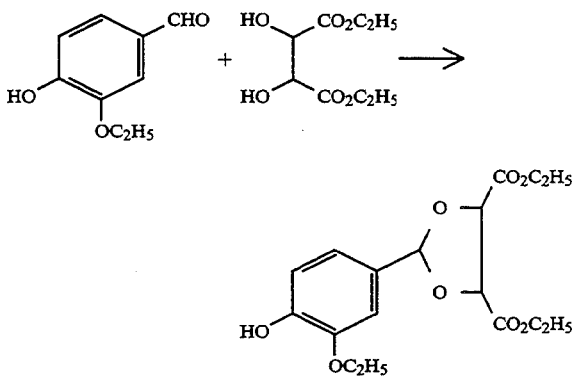

A mixture of diethyl L-tartrate (309 g, 1.5 mol), ethyl vanillin (166 g, 1 mol), toluene (2 L) and p-toluenesulfonic acid (5 g, 0.026 mol) was heated at 115°–116° C. for 24 hours under a nitrogen atmosphere. During the reaction, water was removed by azeotropic distillation via a Dean-Stark trap. The mixture was washed sequentially with saturated sodium bicarbonate solution (500 mL), brine (2×1 L) and dried over sodium sulfate. The solvent was evaporated under reduced pressure and the solid obtained was recrystallized from isopropanol to provide 120 g (34% yield) of (4R,5R)-2-(3-ethoxy-4-hydroxy-phenyl)4,5-dicarboethoxy-1,3-dioxolane, mp 78°–80° C., $[\alpha]_D^{25} -38°$ (c,1.0, methanol). $^1$H-HMR (CDCl$_3$)$\delta$ 7.17 (1H,d,J=1.8 Hz), 7.06 (1H,dd,J=1.8 Hz and 8.10 Hz), 6.91 (1H,d,J=8.2 Hz), 6.07 (1H,s), 5.83 (1H,s), 4.91, (1H,d,J=4.0 Hz), 4.80 (1H,d,J=4.0 Hz), 4.37–4.25 (4H, 2 q, overlapping, J=7.2 Hz), 4.15 (2H,q,J=7.0 Hz), 1.45 (3H,t,J=7.0 Hz), 1.38–1.29 (6H,2 t, overlapping J=7.2 Hz). IR (KBr) 3390, 2980, 2930, 1735, 1600 cm$^{-1}$. MS m/e (% abundance) 354 (55), 326 (3), 281 (40), 182 (85), 167 (85), 154 (100), 137 (70), 110 (30), 93 (10), 81 (10), 53 (5).

Example 2

(4R,5R)-2-(3-Methoxy-4-hydroxy-phenyl)-4,5-dicarboethoxy-1,3-dioxolane

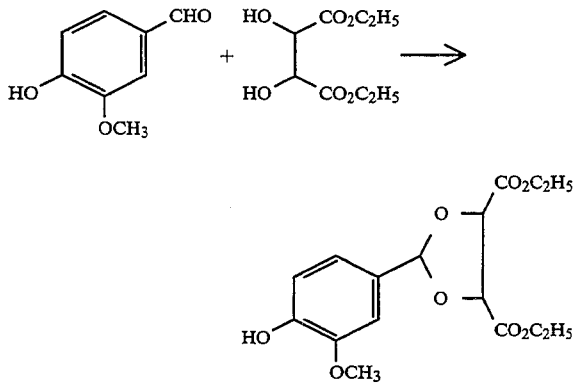

In a fashion similar to that described in Example 1, vanillin was condensed with diethyl L-tartrate to provide (4R,5R)-2-(3-methoxy-4-hydroxy-phenyl)-4,5-dicarboethoxy-1,2-dioxolane, mp 62°–64° C., $[\alpha]_D^{25} -41.7°$ (c, 1.5, methanol). $^1$H-NMR (CDCl$_3$)$\delta$7.20 (1H,d,J=1.8 Hz), 7.03 (1H,dd,J=1.8 Hz and 8 Hz), 6.90 (1H,d,J=8 Hz), 6.09 (1H,s), 5.88 (1H,s), 4.92 (1H,d,J=3.8 Hz), 4.81 (1H,d,J=3.8 Hz), 4.36–4.24 (4H, 2 q, overlapping, J=7.1 Hz), 3.90 (3H,s), 1.38–1.28 (6H, 2 t, overlapping, J=7.1 Hz). IR (KBr) 3500, 2970, 1740, 1605 cm$^{-1}$. MS m/e (% abundance) 340 (2), 267 (14), 168 (100), 151 (95), 137 (50), 109 (10), 65 (10), 43 (6).

Example 3

(4R, 5R)-2-(3,4-Methylenedioxyphenyl)-4,5-dicarboethoxy-1,3-dioxolane

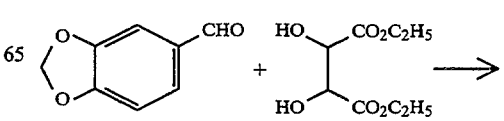

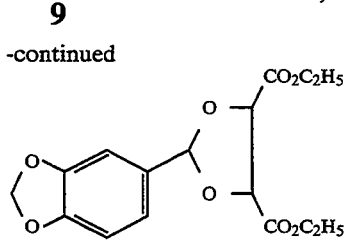

A mixture of piperonal (60 g, 0.4 mol), triethyl orthoformate (59.2 g, 0.4 mol), toluene (250 mL) and p-toluenesulfonic acid (2 g, 0.01 mol) was heated at 100°-110° C. for 0.5 h. Diethyl L-tartrate (103 g, 0.5 mol) was added to the hot solution over a 10 min. period. The mixture was then heated at reflux for 2 h. Subsequently over a 3 hour period, distillate (150 mL) was collected (pot temperature 84° C. to 110° C). The mixture was cooled (25° C.) and washed with sodium bicarbonate solution (2×50 mL) and brine (1×50 mL). Evaporation of solvents under reduced pressure provided 130.7 g of crude product. Recrystallization from methanol provided 90 g (67% yield) of (4R,5R)-2-(3,4-methylenedioxyphenyl)-4,5-dicarboethoxy-1,3-dioxolane, mp 39°-40° C., $[\alpha]_D^{25} -34.8°$ (c, 1.0 methanol). $^1$H-NMR (CDCl$_3$)δ7.12 (1H,d,J=1.5 Hz), 7.03 (1H,dd,J=1.5 Hz and 7.9 Hz), 6.80 (1H,d,J=7.9 Hz), 6.06 (1H,s), 5.97 (2H,s), 4.91 (1H,d,J=4.0 Hz), 4.80 (1H,d,J=4.0 Hz), 4.36–4.26 (4H, 2 q, overlapping, J=7.0 Hz), 1.38–1.30 (6H, 2 t, overlapping, J=7.0 Hz). IR (KBr) 2980, 2900, 1735, 1490, 1445, 1415 cm$^{-1}$. MS m/e (% abundance) 338 (3), 265 (16), 166 (100), 149 (96), 135 (54), 121 (35), 93 (10), 65 (12), 43 (8).

Example 4

(4R,5R)-2-(2-Phenyl-1-ethenyl)-4,5-dicarboethoxy-1,3-dioxolane

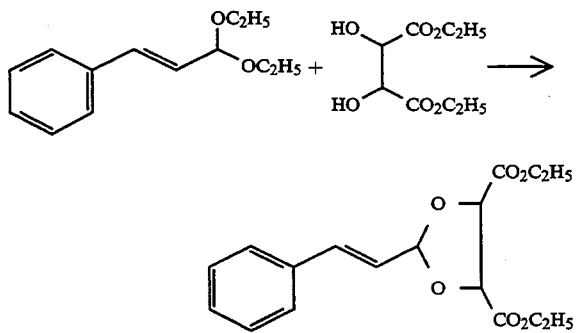

A mixture of cinnamaldehyde diethylacetal (223.0 g, 1.08 mol), diethyl L-tartrate (290 g, 1.41 mol), toluene (1100 g) and pyridinium p-toluenesulfonate (1.7 g) was heated at 92°-110° C. for a 6 hour period. During the heating period, volatiles (250-300 mL) were removed by distillation through an 8″ Vigreaux column. The mixture was cooled (25° C.) and washed with aqueous sodium bicarbonate solution (350 mL) and brine (4×200 mL). Evaporation of solvents and crystallization of the residue gave 250 g (72.3% yield) of (4R,5R)-2-(2-phenyl-1-ethenyl)-4,5-dicarboethoxy-1-3-dioxolane, mp 55.5°-56° C., $[\alpha]_D^{25} -5.2°$ (c,0.1,methanol) $^1$H-NMR (CDCl$_3$)δ7.45-7.26 (5H,m), 6.86 (1H,d, J=16.1 Hz), 6.26 (1H,dd,J=6.8 Hz and 16.1 Hz), 5.82 (1H,d,J=6.8 Hz), 4.87 (1H,d,J=3.6 Hz), 4.78 (1H,d,J=3.6 Hz), 4.36–4.26 (4H,2 q, overlapping J=7.1 Hz), 1.38–1.31 (6H, 2 t, overlapping, J=7.1 Hz). IR(KBr) 2970,2890,1745,1720,1450,1410 cm.$^{-1}$ MS m/e (% abundance) 320(2), 247(6), 148 (38), 131(78), 115(100), 95(80), 91(8), 77(15), 55(14).

Example 5

(4R,5)-2-(4-methoxyphenyl)-4,5-dicarboethoxy-1,3-dioxolane

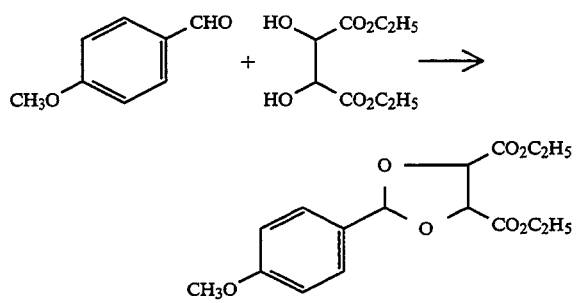

A mixture of triethylorthoformate (108 g, 0.74 mol) anisic aldehyde (89.4 g, 0.66 mol), diethyl L-tartrate (153.1 g, 0.743 mol), dimethylformamide (294 g) and p-toluenesulfonic acid (1.3 g) was heated at 100°-105° C. for 4 h. During the next 5 h, low boiling materials (100 mL) were removed by distillation (maximum pot temperature: 100° C., 300-360 mm vacuum). Sodium acetate (0.62 g) was added. Most of the dimethylformamide was then removed under reduced pressure (10 mm, maximum pot temperature 110° C.). The residue was cooled (25° C.) and diluted with toluene (500 mL). The mixture was washed with aqueous sodium bicarbonate (100 mL) and with brine (3×200 mL). Removal of solvents gave 211 g of crude product. Chromatography of a portion of the crude product followed by Kugelrohr distillation (0.5 mm, bath temperature 240°-250° C.) gave a sample of (4R,5R)-2-(4-methoxyphenyl)-4,5-dicarboethoxy-1,3-dioxolane, GLC purity: 98.6% $[\alpha]_D^{25} -31.6°$ (c,1.14,ethanol). $^1$H-NMR (CDCl$_3$)δ7.52 (2H,d,J=7.5 Hz), 6.91 (2H,d,J=7.5 Hz), 6.11 (1H,s), 4.92 (1H,d,J=4.0 Hz), 4.81 (1H,d,J=4.0 Hz), 4.37–4.25 (4H, 2 q, overlapping, J=7.2 Hz), 3.81 (3H,s), 1.38–1.29 (6H, 2 t, overlapping, J=7.2 Hz). IR (KBr) 2980, 1750, 1610, 1590, 1510 cm.$^{-1}$ MS m/e (% abundance) 324 (2), 251(12, 152(92), 135(100), 121(40), 108(16), 91(5), 77(14), 51(5).

Example 6

(4R,5R)-2-(4-Methylphenyl)-4,5-dicarboethoxy-1,3-dioxolane

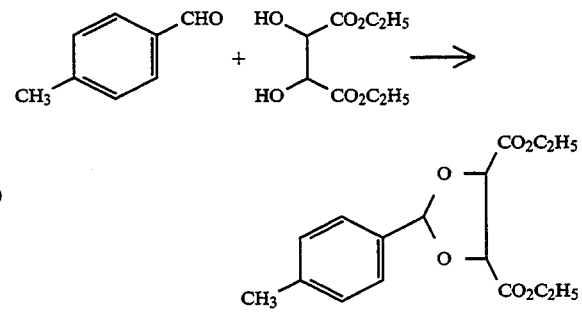

In a fashion similar to that described in Example 3, p-tolualdehyde was condensed with diethyl L-tartrate to provide (4R,5R)-2-(4-methylphenyl)-4,5-dicarboethoxy-1,3-dioxolane, an oil, GLC analysis: 93%, $[\alpha]_D^{25} -9.6°$ (c,0.1,methanol), $^1$H-NMR (CDCl$_3$)δ7.47 (2H,d,J=8.0 Hz), 7.18 (2H,d,J=8.0 Hz) 6.12 (1H,s), 4.93 (1H,d,J=4.0 Hz), 4.81 (1H,d,J=7.2 Hz), 4.34-4.22 (4H,2 q, overlapping, J=7.2 Hz), 2.34 (3H, s), 1.35-1.26 (6H 2 t, overlapping, J=7.2 Hz). IR (film) 2980, 1740, 1615 cm$^{-1}$. MS m/e (% abundance) 308(2), 293(1), 279(1), 235(12), 136(68), 119(100), 105(50), 91(20), 77(8), 43(6).

Example 7

(4R5R)-2-(3-Methoxy-4-hydroxy-phenyl)-4,5-dicarbomethoxy-1,3-dioxolane

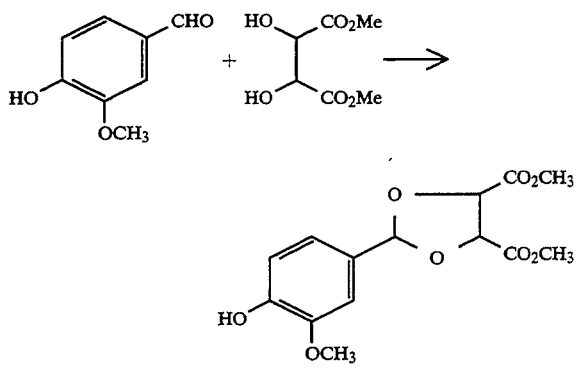

In a fashion similar to that described for Example 3, vanillin and dimethyl L-tartrate were condensed to provide (4R, 5R)-2-(3-methoxy-4-hydroxy-phenyl)-4,5-dicarbomethoxy-1,3-dioxolane, mp 88°-90° C., $[\alpha]_D^{25} -35.1°$ (c,0.1,methanol). $^1$H-NMR (CDCl$_3$)δ7.20 (1H,d,J=1.8 Hz), 7.06 (1H,dd,J=1.8 Hz and 8.2 Hz), 6.19 (1H,d,J=8.2 Hz), 6.08 (1H,s), 5.82 (1H, s), 4.96 (1H,d,J=3.8 Hz), 4.85 (1H,d,J=3.8 Hz), 3.91 (3H,s), 3.87 (3H,s), 3.84 (3H,s). IR (film) 3450, 1750, 1600, 1510, 1460, 1430 cm$^{-1}$. Ms m/e (% abundance) 313(2), 312(12), 253(40), 168(84), 151(100), 124(22), 109(14), 59(18).

Example 8

(E)-(4R,5R)-2-(1-Hexyl-2-phenyl-1-ethenyl)-4,5-dicarbomethoxy-1,3-dioxolane

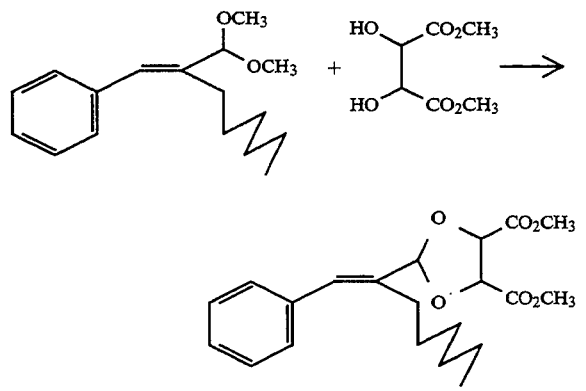

In a fashion similar to that described in Example 4, α-hexylcinnamaldehyde dimethyl acetal and dimethyl L-tartrate were condensed to provide a mixture of (E)- and (Z)-(4R,5R)-2-(1-hexyl-2-phenyl-1-ethenyl)-4,5-dicarbomethoxy-1,3-dioxolane in an approximate ratio of 90:10 Crystallization provided the pure E-isomer, mp 49°-50° C., $[\alpha]_D^{25} -2.2$ (c,0.2, methanol). $^1$H-NMR (CDCl$_3$)δ7.35-7.26 (5H,m), 6.74 (1H,s), 5.84 (1H,s), 4.86 (1H,d,J=4.4 Hz), 4.70 (1H,d,J=4.4 Hz), 3.85 (3H,s), 3.80 (3H,s), 2.34-2.27 (2H,m), 1.58-1.55 (2H,m), 1.37-1.26 (6H,m), 0.93-0.87 (3H,m). IR (KBr)2900, 2840, 1730, 1430, 1340, 1200, 1100, 1060, 1030, 980, 950, 915, 870, 790, 750, 730, 690 cm$^{-1}$. MS m/e (% abundance) 305 (4), 292 (17), 291 (100), 145 (18), 142 (25), 131 (73), 129 (76), 128 (26), 117 (74), 116 (17), 115 (51), 104 (29), 91 (57), 59 (31), 41 (25).

Example 9

(E)-(4R,5R)-2-(1-Hexyl-2-phenyl-1ethenyl)-4,5-dicarboethoxy-1,3-dioxolane

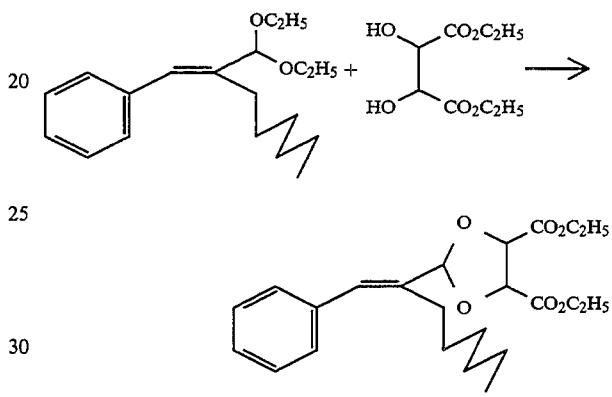

In a fashion similar to that described in Example 4, α-hexylcinnamaldehyde diethyl acetal and diethyl L-tartrate were condensed to provide a mixture of (E)- and (Z)-(4R,5R)-2-(1-hexyl-2-phenyl-1-ethenyl)-4,5-dicarboethoxy-1,3-dioxolane. Low temperature crystallization provided the pure E-isomer, $[\alpha]_D^{25} -5.9$ (c,0.1,methanol). $^1$H-NMR(CDCl$_3$)δ7.35-7.26 (5H,m), 6.75 (1H,s), 5.65 (1H,s), 4.87 (1H,d,J=4.5 Hz), 4.74 (1H,d,J=4.5 Hz), 4.36-4.25 (4H,2 q, overlapping, J=7.1 Hz), 2.38-2.32 (2H,m), 1.58-1.57 (2H,m), 1.38-1.25 (6H,2 t, overlapping, J=7.1 Hz), 1.38-1.22 (6H,m) 0.88-0.83 (3H,m). IR (film) 2900, 2840, 1750, 1450, 1360, 1260, 1200, 1100, 1010, 940, 900, 840, 730, 680 cm$^{-1}$. MS m/e (% abundance) 404 (0.6), 333 (4), 320 (18), 319 (100), 143 (21), 142 (38), 131 (80), 129 (88), 128 (28), 117 (78), 115 (52), 104 (31), 91 (56), 43 (27).

Example 10

Preparation of a Vanillin Cigarette

A 1% ethanolic solution of the compound from Example 1 was applied to cigarette papers at the rate of 100 ppm. The paper was incorporated into cigarettes. Prior to smoking, no odor of vanillin was observed. Upon smoking a strong, distinctly vanillin odor was observed in the room air.

Example 11

Preparation of a Cigarette Containing Vanillin Flavored Tobacco

A 1% ethanolic solution of the product of Example 1 was injected into the tobacco of a typical American Blend cigarette at a level of 100 ppm. Prior to smoking, no odor of vanillin was observed. Upon smoking, the mainstream and sidestream smoke displayed a strong vanillin odor.

Example 12

Preparation of n α-Hexyl Cinnamic Aldehyde Cigarette

A 1% ethanolic solution of the compound from Example 8 was applied to cigarette papers at the rate of 100 ppm. The paper was incorporated into cigarettes. Prior to smoking, no odor of α-hexyl cinnamic aldehyde was observed. Upon smoking a slight (but distinct), pleasant jasmine-like floral odor was observed in the room air.

Example 13

Preparation of Cinnamon Tea

The compound from Example 4 was added to tea bags containing unflavored green tea at the rate of 100 ppm. The tea bags had no cinnamon odor. On seeping, the headspace developed a distinct cinnamon aroma which provided a more pleasant tea.

We claim:

1. An organoleptic composition, comprising:
   (a) a dicarboalkoxy dioxolane derivative represented by the formula:

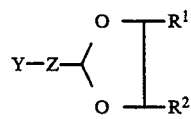

wherein $R^1$ and $R^2$ may be the same or different and are represented by the formula $-CO_2R^3$, wherein $R^3$ is selected from the group consisting of hydrogen and lower alkyl, provided that in at least one of $R^1$ and $R^2$, $R^3$ is lower alkyl; Z is a direct bond or $-CH=C(R^4)-$, wherein $R^4$ is n-hexyl; and Y is represented by the formula:

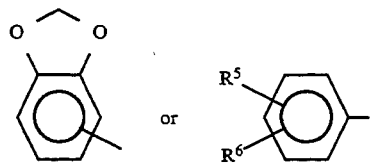

wherein $R^5$ and $R^6$ may be the same or different and are selected from the group consisting of lower alkyl and $-OR^7$, wherein $R^7$ is selected from the group consisting of hydrogen and lower alkyl; and
   (b) an organoleptic agent;
   wherein the dicarboalkoxy dioxolane derivative is present in the organoleptic composition in an amount such that, when the dicarboalkoxy dioxolane derivative is subjected to hydrolysis, pyrolysis or both, the dicarboalkoxy dioxolane derivative provides an organoleptically effective level of flavor or aroma.

2. The organoleptic composition according to claim 1, wherein the dicarboalkoxy dioxolane derivative has the name:
   2-(3-Ethoxy-4-hydroxy-phenyl)-4,5-dicarboethoxy-1,3-dioxolane
   2-(3-Methoxy-4-hydroxy-phenyl)-4,5-dicarboethoxy-1,3-dioxolane
   2-(4-Methoxyphenyl)-4,5-dicarboethoxy-1,3-dioxolane
   2-(4-Methylphenyl)-4,5-dicarboethoxy-1,3-dioxolane
   2-(3,4-Methylenedioxyphenyl)-4,5-dicarboethoxy-1,3-dioxolane
   2-(2-phenyl-1-ethenyl)-4,5-dicarboethoxy-1,3-dioxolane
   2-(3-Methoxy-4-hydroxy-phenyl)-4,5-dicarbomethoxy-1,3-dioxolane
   2-(1-Hexyl-2-phenyl-1-ethenyl)-4,5-dicarbomethoxy-1,3-dioxolane
   2-(1-Hexyl-2-phenyl-1-ethenyl)-4,5-dicarboethoxy-1,3-dioxolane.

3. The organoleptic composition according to claim 2, wherein the dicarboalkoxy dioxolane derivative has the name:
   (4R, 5R)-2-(3-Ethoxy-4-hydroxy-phenyl)-4,5-dicarboethoxy-1,3-dioxolane
   (4R, 5R)-2-(3-Methoxy-4-hydroxy-phenyl)-4,5-dicarboethoxy-1,3-dioxolane
   (4R, 5R)-2-(4-Methoxyphenyl)-4,5-dicarboethoxy-1,3-dioxolane
   (4R, 5R)-2-(4-Methylphenyl)-4,5-dicarboethoxy-1,3-dioxolane
   (4R, 5R)-2-(3,4-Methylenedioxyphenyl)-4,5-dicarboethoxy-1,3-dioxolane
   (4R, 5R)-2-(2-Phenyl-1-ethenyl)-4,5-dicarboethoxy-1,3-dioxolane
   (4R, 5R)-2-(3-Methoxy-4-hydroxy-phenyl)-4,5-dicarbomethoxy-1,3-dioxolane
   (E)-(4R, 5R)-2-(1-Hexyl-2-phenyl-1-ethenyl)-4,5-dicarbomethoxy-1,3-dioxolane
   (E)-(4R, 5R)-2-(1-Hexyl-2-phenyl-1-ethenyl)-4,5-dicarboethoxy-1,3-dioxolane.

4. The organoleptic composition according to claim 3, wherein the dicarboalkoxy dioxolane derivative has the name:
   (4R, 5R)-2-(3-Ethoxy-4-hydroxy-phenyl)-4,5-dicarboethoxy-1,3-dioxolane
   (4R, 5R)-2-(3-Methoxy-4-hydroxy-phenyl)-4,5-dicarboethoxy-1,3-dioxolane
   (4R, 5R)-2-(2-Phenyl-1-ethenyl)-4,5-dicarboethoxy-1,3-dioxolane
   (E)-(4R, 5R)-2-(1-Hexyl-2-phenyl-1-ethenyl)-4,5-dicarbomethoxy-1,3-dioxolane
   (E)-(4R, 5R)-2-(1-Hexyl-2-phenyl-1-ethenyl)-4,5-dicarboethoxy-1,3-dioxolane.

* * * * *